United States Patent [19]
Mori et al.

[11] Patent Number: 5,488,134
[45] Date of Patent: Jan. 30, 1996

[54] PREPARATION OF COMPOUNDS OF LIGNAN SERIES

[75] Inventors: Sachio Mori, Ashiya; Shozo Takechi, Higashiosaka; Shiro Kida, Osaka, all of Japan

[73] Assignee: Shionogi & Co., Ltd., Osaka, Japan

[21] Appl. No.: 356,199

[22] PCT Filed: Apr. 12, 1994

[86] PCT No.: PCT/JP94/00612

§ 371 Date: Dec. 16, 1994

§ 102(e) Date: Dec. 16, 1994

[87] PCT Pub. No.: WO94/24087

PCT Pub. Date: Oct. 27, 1994

[30] Foreign Application Priority Data

Apr. 16, 1993 [JP] Japan ................... 5-089944

[51] Int. Cl.[6] .................................................. C07L 69/76
[52] U.S. Cl. ............................................. 560/53; 560/52
[58] Field of Search ................................ 560/53, 52

[56] References Cited

PUBLICATIONS

Gokhale et al., "An Efficient Synthesis of Naphthalenic Lignan Lactones", *Indian Journal of Chemistry*, vol. 26B, Nov. 1987, pp. 1030–1034.

Iwao et al., "Generation and Diels–Alder Reaction of 1–Siloxy–3–Arylisobenzofurans from 3–Arylphthalides", *Chemistry Letters*, pp. 1263–1266, 1984.

*Primary Examiner*—Paul J. Killos
*Attorney, Agent, or Firm*—Wenderoth, Lind & Ponack

[57] ABSTRACT

This invention relates to a process for preparation of the compounds of lignan series in a regioselective manner. This invention provide a process for preparing a compound of the formula (I):

which process is characterized by that a lactone compound represented by the formula (II) is allowed to react with a compound of the formula: $R^7Cl$ in the presence of a base, then the resulting compound is subjected to addition reaction with an acetylenic compound of the formula (III), then the resulting compound is reduced;

in which $R^1$ is alkyl, cycloalkyl, cycloalkyl lower alkyl, or aralkyl and the like; $R^2$ and $R^3$ each is lower alkoxy and the like; $R^4$ is lower alkoxy or hydrogen; and $R^5$ and $R^6$ each is lower alkyl; and $R^7$ is tri(lower alkyl)silyl.

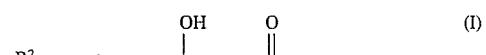

(I)

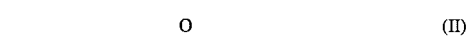

(II)

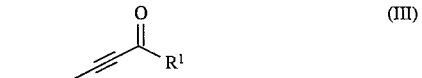

(III)

9 Claims, No Drawings

PREPARATION OF COMPOUNDS OF LIGNAN SERIES

This Application is a 371 of PCT/JP94/00612 Apr. 12, 1995.

The present invention relates to a novel method of preparing compounds of lignan series. More particularly, it relates to a method of preparing compounds of lignan series having an aryl ketone chain or an alkyl ketone chain and to a method of preparing said compounds of lignan series utilizing Diels-Alder reaction.

The compounds of lignan series are useful for treating arteriosclerosis, particularly atherosclerosis, and various compounds were disclosed and claimed already by the present inventors (Japanese Patent Publication (Kokai) 5-310634, and WO 93/08155).

The present invention relates to a process for preparing a compound represented by the formula (I)

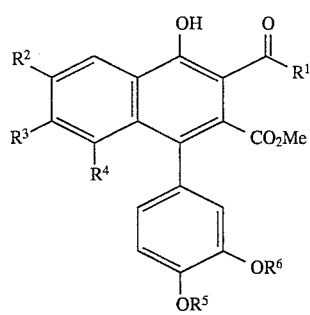

in which $R^1$ is alkyl, cycloalkyl, cycloalkyl-lower alkyl, aralkyl, or optionally-substituted aryl;

each of $R^2$ and $R^3$ is lower alkoxy or $R^2$ and $R^3$ are combined together to form an alkylenedioxy;

$R^4$ is lower alkoxy or hydrogen; and each of $R^5$ and $R^6$ is lower alkyl;

which process is characterized by that a lactone compound represented by the formula (II)

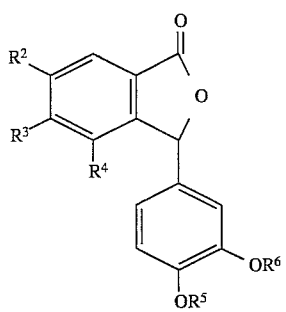

in which $R^2$, $R^3$, $R^4$, $R^5$, and $R^6$ are as defined above, is allowed to react with a compound of the formula: $R^7Cl$, wherein $R^7$ is tri (lower alkyl)silyl, in the presence of a base, and then the resulting compound is subjected to addition reaction with an acetylenic compound of the formula (III)

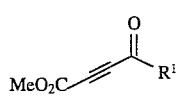

in which $R^1$ is as defined above, to give a compound represented by the formula (IV)

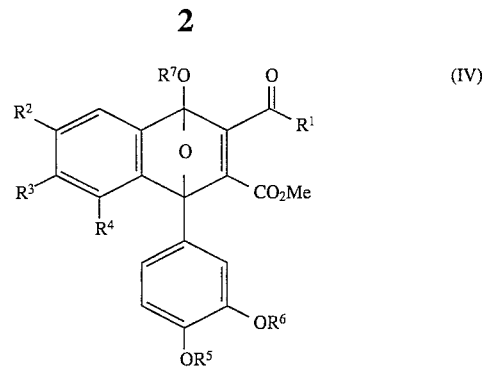

in which $R^1$, $R^2$, $R^3$, $R^4$, $R^5$, $R^6$ and $R^7$ are as defined above, which is then reduced.

In the present invention, it is particularly preferred when $R^1$ is phenyl which is optionally substituted with halogen, trihalomethyl, lower alkoxy or lower alkyl because the aimed compound can be prepared with good regioselectivity. For example, the reaction is expressed by the following scheme (See Example 1 hereinafter).

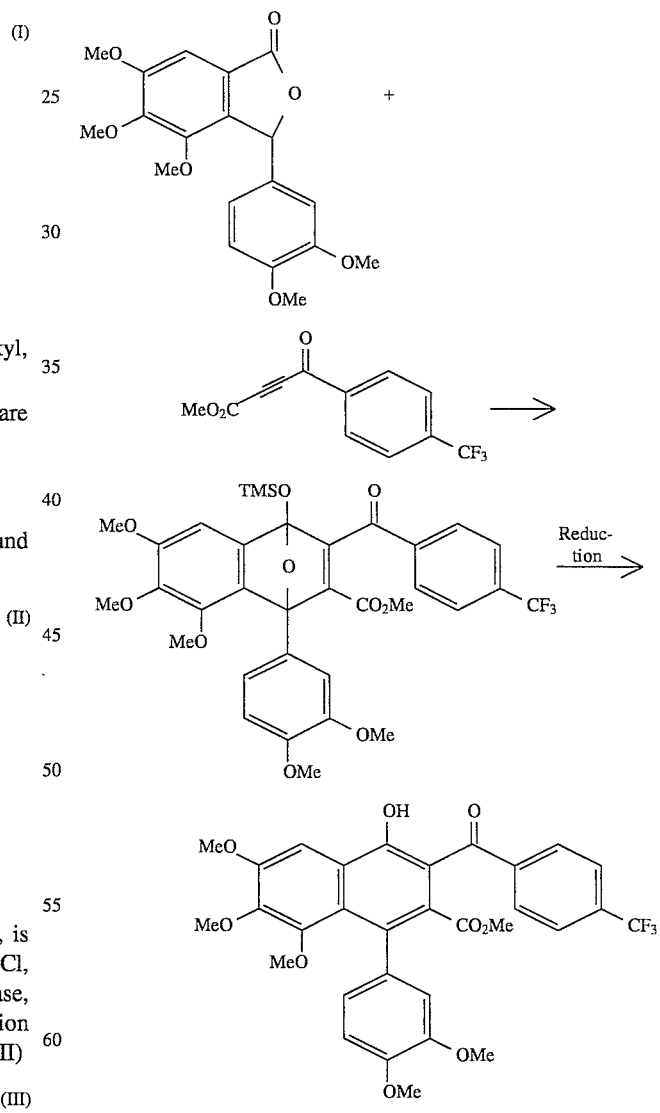

In the above-mentioned reaction formulae, two types of products will be produced in the addition reaction. The selectivity for the aimed compound given in the reaction formulae versus the side product which is a positional isomer is high in terms of regioselectivity such as, for example, 8.4:1 in the case of Example 1, 11:1 in the case of Example 4 and 13:1 in the case of Example 5 as will be described hereinafter. As such, it is now possible to prepare the aimed compound with high selectivity when $R^1$ is an aryl and the method of the present invention is a practical method for a large scale synthesis of lignan analogues having an aryl ketone chain.

In the specification, the term "lower alkoxy" for $R^2$, $R^3$ and $R^4$ means oxy group substituted with "lower alkyl" which is mentioned later and its preferred example is methoxy. The term "alkylenedioxy" for $R^2$ and $R^3$ is $C_1$ to $C_3$ alkylenedioxy such as methylenedioxy, ethylenedioxy and propylenedioxy.

The term "tri(lower alkyl)silyl" for $R^7$ means a silyl group substituted with three groups which may be the same or different, which are selected from the "lower alkyl" mentioned later and, the examples therefor are trimethylsilyl and tert-butyldimethylsilyl.

The term "alkyl" for $R^1$ means $C_1$ to $C_{10}$ alkyl while "lower alkyl" means linear or branched $C_1$ to $C_6$ alkyl such as methyl, ethyl, n-propyl, isopropyl, n-butyl, isobutyl, sec-butyl, n-pentyl, 1-ethylpropyl and 2-ethylbutyl. The term "lower alkyl" for $R^5$ and $R^6$ has the same meaning. The term "cycloalkyl" means $C_5$ to $C_7$ cycloalkyl such as cyclopentyl, cyclohexyl and cycloheptyl. The term "cycloalkyl lower alkyl" means a group in which the above-defined lower alkyl has the above-defined cycloalkyl substituent and its examples are cyclohexylmethyl and cyclopentylethyl. The term "aralkyl" means a group in which a lower alkyl which is substituted with an aryl and its examples are benzyl, p-methoxybenzyl, phenylethyl, phenylpropyl and naphthylmethyl.

The term "optionally-substituted aryl" means , for example, phenyl or naphthyl which may be substituted with halogen, trihalomethyl, lower alkoxy or lower alkyl. Preferred examples are phenyl with one halogen substituent (more preferably, 4-chlorophenyl, etc.), phenyl with one trihalomethyl substituent (more preferably, 4-(trifluoromethyl)phenyl, etc.), phenyl with one lower alkoxy substituent (more preferably, 2-methoxyphenyl, etc.) and phenyl with one lower alkyl substituent (more preferably, 2-methylphenyl, etc.).

The method of the present invention is composed of the following steps.

Step 1

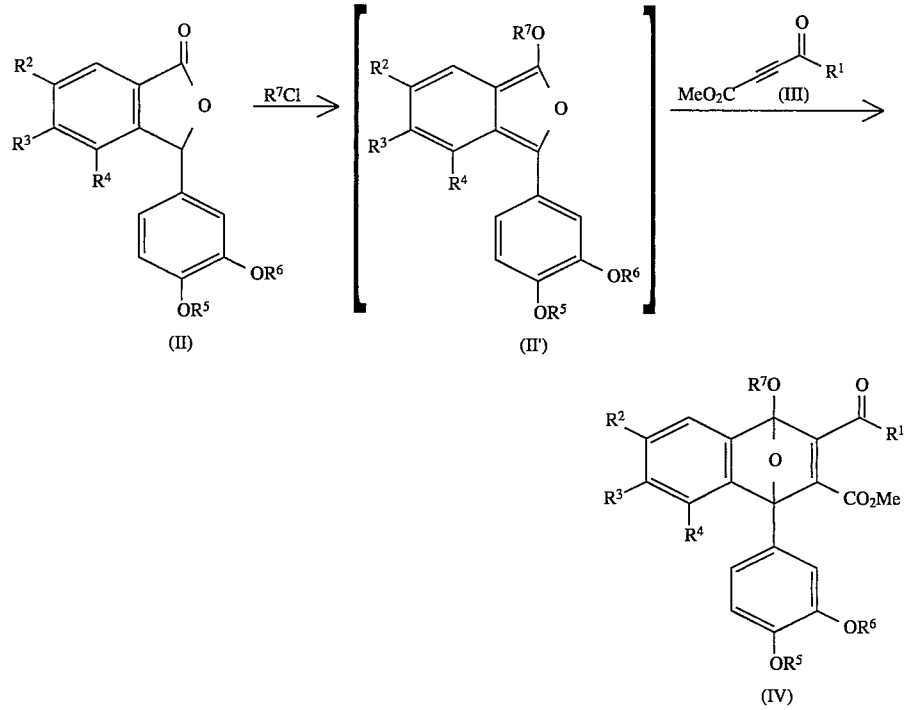

Step 2

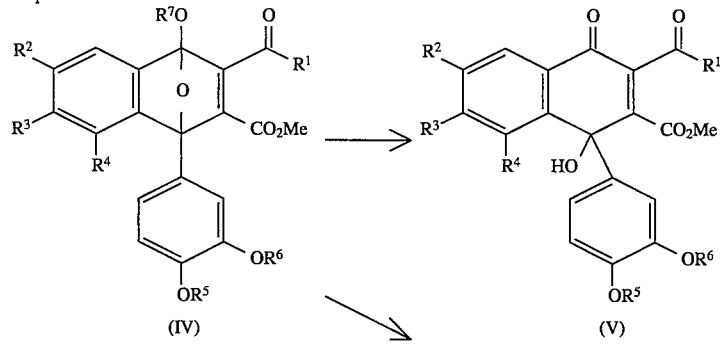

Step 3

[Chemical scheme: Compound (V) → Compound (I)]

SUMMARY OF EACH STEP

The first step is a step in which a lactone compound (II) is made into an enolate using a base, then the enolate is trapped using a silyl compound ($R^7$ Cl) which is an electrophile and the resulting compound is subjected to a reaction with an acetylenic compound (III) in situ, to synthesize a compound (IV). An isobenzofuran compound (II') which may be an intermediate need not be isolated, and therefore, the reaction can be conducted in situ successively.

The second step is a step in which the tri(lower alkyl) silyloxy ($OR^7$) of the compound (IV) is deprotected using an acid to synthesize a hydroxydiketone compound (V).

The third step is a step in which the compound (V) is reduced using a metal or a metal salt with low valence in the presence of an acid to synthesize a compound (I).

Alternatively, it is possible to produce a compound (I) by subjecting a product (IV) of the first step directly to the reaction under the same condition for the third step by eliminating the second step.

Reaction Conditions

There is no particular limitation as to the ratio of the compounds (II) to (III) used in the first step, but the compound (III) is usually used in an equivalent or excess amount to the compound (II), preferably in the ratio between 1:1 and 1:1.5. The ratio of the silyl compound ($R^7$Cl) to the compound (II) is similar to this.

Examples of the base used are ordinary dialkyl metal amide such as lithium diisopropylamide and sodium diethylamide, etc., and bis(trialkylsilyl) metal amides such as lithium bis(trimethylsilyl)amide, potassium bis(trimethylsilyl)amide and sodium bis(triethylsilyl)amide, etc. Preferably, lithium bis(trimethylsilyl)amide is used.

With regard to the solvent for the reaction, ethers (e.g. tetrahydrofuran, diethyl ether and dioxane), hydrocarbons (e.g. n-hexane), aromatic hydrocarbons (e.g. benzene and toluene) and halogenated hydrocarbons (e.g. methylene chloride) may be used either solely or in combination. Preferably, a mixture of tetrahydrofuran and methylene chloride is used.

The reaction of this step is completed usually at −100° C.–100° C. (preferably at −80° C.–20° C.) within several minutes to several hours.

Examples of the acid used in the second step are organic acids (e.g. formic acid, acetic acid and trifluoroacetic acid) and inorganic ones (e.g. boric acid, hydrochloric acid and sulfuric acid) which are commonly used. Preferably, sulfuric acid is used.

With regard to the solvent for the reaction, ethers (e.g. tetrahydrofuran and dioxane) and alcohols (e.g. methanol and ethanol) may be used together with water either solely or in combination and, preferably, aqueous dioxane is used. Required amount of water is about one mole equivalent versus the compound (IV).

The reaction of this step is usually carried out at 0° C.–100° C. (preferably at 20° C.–50° C.) and completed within several minutes to several hours.

Examples of the acid used in the third step are inorganic acids (e.g. hydrochloric acid and sulfuric acid) which are commonly used. Preferably, hydrochloric acid is used.

With regard to the metal, tin, zinc, iron, etc. may be used and, with regard to the metal salt with low valence, stannous chloride, titanium trichloride, ferrous chloride, etc. may be used. Preferably, titanium trichloride is used.

With regard to the solvent for the reaction, ethers (e.g. tetrahydrofuran and dioxane) and alcohols (e.g. methanol and ethanol) may be used in the presence or absence of water either solely or in combination. Preferably, a mixed solvent of dioxane with methanol is used.

The reaction of this step is usually carried out at temperatures between 0° C. and 100° C. (preferably at 20° C.–70° C.) and completed within several minutes to several hours.

The present invention will be further illustrated by way of the following referential examples and working examples which, however, are not intended to limit the scope of the present invention.

SYNTHETIC EXAMPLES OF THE COMPOUND (II)

PREPARATION 1

Synthesis of 3-(3,4-Dimethoxyphenyl)-4,5,6-trimethoxy-1(3H)-isobenzofuranone: II-1

Step 1

Synthesis of 4,4-dimethyl-2-(3,4,5-trimethoxyphenyl)-2-oxazoline: 2

A solution of 16.2 g (70 mmoles) of 3,4,5-trimethoxybenzoyl chloride (compound 1) in 40 ml of dry methylene chloride was added dropwise to a solution of 12.5 g (140 mmoles) of 2-amino-2-methyl-1-propanol in 50 ml of dry methylene chloride under cooling in an ice-bath for 30 minutes. After completion of the addition, the mixture was stirred for additional 45 minutes and the reaction solution was filtered through a glass filter. The filtered cake was washed with methylene chloride and the filtrate was combined with the washing, which was followed by concentration in vacuo. The residue was dissolved in 30 ml of dry toluene, and 6.64 ml (91.0 mmoles) of thionyl chloride was added dropwise thereto under cooling in an ice-bath. The mixture was allowed to warm to room temperature, while being stirred for additional 45 minutes. Subsequently, 20 g of ice and aqueous sodium hydroxide (18 g of NaOH in 60 ml of water) were added to the mixture and then the mixture was extracted with toluene. The extract was washed with water and brine and dried over anhydrous magnesium sulfate. After concentration in vacuo, the residue was crystallized from 70 ml of n-hexane to give 16.8 g (90.6% from compound 1) of the desired compound. Melting point: 87°–89° C.

$^1$H-NMR:δ(CDCl$_3$) 1.39 (6H,s) 3.88 (3H,s) 3.91 (6H,s) 4.10 (2H,s) 7.20 (2H,s).

Step 2

Synthesis of the Compound II-1

Under nitrogen flow, a 1.68N hexane solution of n-butyllithium (40.0 ml; 67.2 mmoles) was added dropwise over 15 minutes to a solution of 16.8 g (63.4 mmoles) of compound 2 in 100 ml of dry THF, which was cooled with a refrigerant at −30° C. After completion of the addition, the mixture was stirred for additional 45 minutes at the same temperature, cooled to −78° C. and a solution of 11.6 g (69.7 mmoles) of 3,4-dimethoxybenzaldehyde in 30 ml of dry THF was added dropwise thereto. The mixture was allowed to warm to room temperature while being stirred for 1 hour, then 20 ml of saturated aqueous ammonium chloride and 20 ml of water were added thereto and the mixture was extracted with ethyl acetate. The extract was washed with water and brine, dried over anhydrous magnesium sulfate, and concentrated in vacuo. The residue was dissolved in 70 ml of 10% sulfuric acid and heated under reflux for 30 minutes. Ice water was added to the reaction solution and the mixture was extracted with methylene chloride. The extract was dried over anhydrous magnesium sulfate, concentrated in vacuo, and the residue was crystallized from 80 ml of methanol to give 20.6 g (90.4% from compound 2) of the desired compound II-1. Melting point: 141°–142° C.

$^1$H-NMR:δ(CDCl$_3$) 3.52 (3H,s) 3.83 (3H,s) 3.89 (3H,s) 3.92 (3H,s) 3.95 (3H,s) 6.32 (1H,s) 6.72 (1H,s) 6.86 (2H,s) 7.21 (1H,s).

The above reaction of Preparation 1 is expressed by the following scheme.

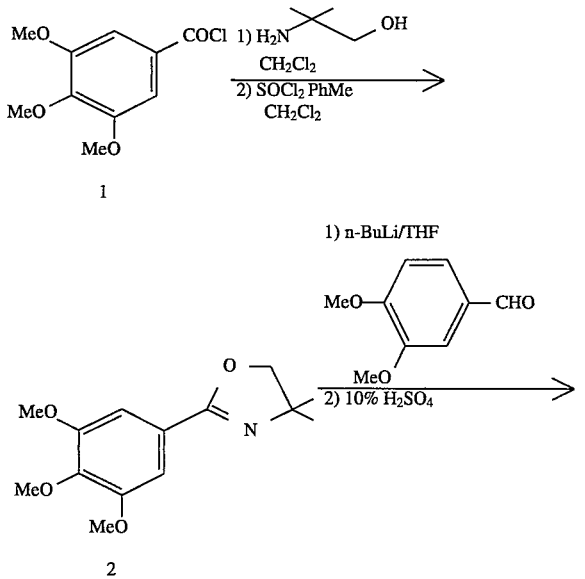

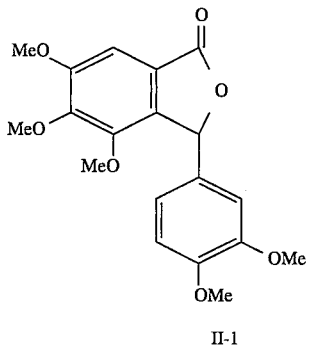

PREPARATION 2

Synthesis of 3-(3,4-Dimethoxyphenyl)-5,6-methylenedioxy-1(3H)-isobenzofuranone: II-2

Step 1

Synthesis of 2-(3,4-Dimethoxy-α-hydroxybenzyl)-4,5-methylenedioxybenzaldehyde ethylenedioxyacetal: 4 i) To a solution of 28.0 g (122 mmoles) of 2-bromo-4,5methylenedioxybenzaldehyde (compound 3) in 250 ml of benzene were added ethylene glycol (14 ml) and 465 mg of p-toluenesulfonic acid and the mixture was heated under reflux for 3 hours to effect dehydration by using a Dean-Stark trap. After cooling in an ice-bath, saturated aqueous sodium bicarbonate was added to the reaction solution and the mixture was extracted with ethyl acetate. The extract was washed with water and brine, dried over anhydrous magnesium sulfate, and concentrated in vacuo to give 33.2 g of a crude product of the acetal as crystals. This was used in the next reaction without further purification.

ii) Under nitrogen flow, a 1.64N solution of n-butyllithium in n-hexane (80 ml) (131 mmoles) was added dropwise to a solution of 33.2 g of the crude acetal obtained above in 300 ml of dry THF at −78° C. After additional stirring for 30 minutes at the same temperature, a solution of 20.3 g (122 mmoles) of 3,4-dimethoxybenzaldehyde in 85 ml of dry THF was added and the mixture was stirred for additional 30 minutes. Saturated aqueous ammonium chloride was added to the reaction solution and the mixture was extracted with ethyl acetate. The extract was washed with water and brine, dried over anhydrous magnesium sulfate, and concentrated in vacuo. The residue was purified by a medium-pressure silica gel column chromatography (600 g of SiO$_2$; ethyl acetate:n-hexane=1:2 to 1:1) to give 35.6 g (80.9% from compound 3) of the desired compound 4 as an oil.

$^1$H-NMR:δ(CD$_3$OD) 3.77 (3H, s) 3.80 (3H, s) 3.90 -4.17 (4H, m) 5.91 (1H, d, J=1.2 Hz) 5.93 (1H, d, J=1.2 Hz) 5.97 (1H, s) 6.13 (1H, 6.85 (1H, s) 6.87 (1H, s) 6.88 (1H, s)6.98 (1H, s) 7.02 (1H, s).

Step 2

Synthesis of 2-(3,4-Dimethoxy-α-acetoxybenzyl)-4,5-methylenedioxybenzaldehyde: 5 i). Under nitrogen flow, acetic anhydride (12.1 ml; 128 mmoles) was added to a solution of 35.6 g (98.3 mmoles) of compound 4 obtained above, 360 mg of N,N-dimethylaminopyridine and 21 ml of triethylamine in 170 ml of dry THF under cooling in an ice-bath. The mixture was allowed to warm to room temperature while being stirred for 50 minutes. Methanol (4.4 ml) was added thereto, the mixture was stirred for 20 minutes, and concentrated in vacuo. Water was added to the residue and the mixture was extracted with ethyl acetate. The extract was washed with water and brine, dried over anhydrous magnesium sulfate and concentrated in vacuo to give 39.6 g of a crude product of the desired acetate as an oil. This was used in the following reaction without further purification.

ii) To a solution of 39.6 g of the crude product of the acetate obtained above in 350 ml of acetone was added 35 ml of 1N hydrochloric acid under cooling in an ice-bath. The mixture was allowed to warm to room temperature while being stirred for 1 hour. The reaction mixture was neutralized by addition of saturated aqueous sodium bicarbonate and concentrated in vacuo. Water was added to the residue and the mixture was extracted with ethyl acetate. The extract was washed with water and brine, dried over anhydrous magnesium sulfate and concentrated in vacuo to give 39.0 g of a crude product of the desired aldehyde 5 as an oil. This was used in the next reaction without further purification.

$^1$H-NMR:δ(CDCl$_3$) 2.16 (3H, s) 3.85 (6H, s) 6.09 (2H, s) 6.80– 6.89 (3H, m) 7.09 (1H, s) 7.32 (1H, s) 7.58 (1H, s).

Step 3

Synthesis of Compound II-2

The crude product (39.0 g) of aldehyde 5 obtained above was dissolved in a mixture of 500 ml of methanol and 250 ml of dioxane and then 130 ml of 2-methyl-2-butene was added thereto. Then, an aqueous solution of 44 g (486 mmoles) of sodium chlorite and 57 g (365 mmoles) of sodium dihydrogenphosphate dihydrate in 250 ml of water was added thereto and the mixture was stirred at room temperature for 20 minutes. After addition of 5N aqueous sodium hydroxide (160 ml) to the reaction solution, the mixture was stirred for 25 minutes, and then 160 ml of 6N hydrochloric acid was added, which was followed by stirring for additional 20 minutes. Ice water was added to the reaction solution and the mixture was extracted with methylene chloride. The extract was washed with water, saturated aqueous sodium bicarbonate and brine, and dried over anhydrous magnesium sulfate. After concentration in vacuo, the crystalline crude residue was washed with ether, and then recrystallized from methanol to give 27.0 g (86.2% from the compound 4) of the desired lactone II-2 as crystals. Melting point: 176°–178° C. (methanol).

$^1$H-NMR:δ(CDCl3) 3.83 (3H, s) 3.89 (3H, s) 6.12 (2H, ABtype, J= 1.2 Hz) 6.20 (1H, s) 6.66 (2H, d, J=1.2 Hz) 6.86 (1H, s) 6.87 (1H, s) 7.25 (1H, s).

The above reaction of Preparation 2 is expressed by the following scheme.

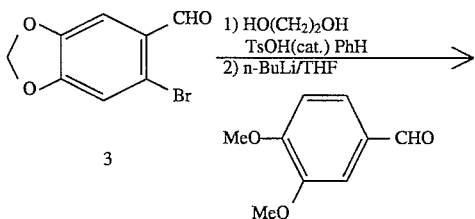

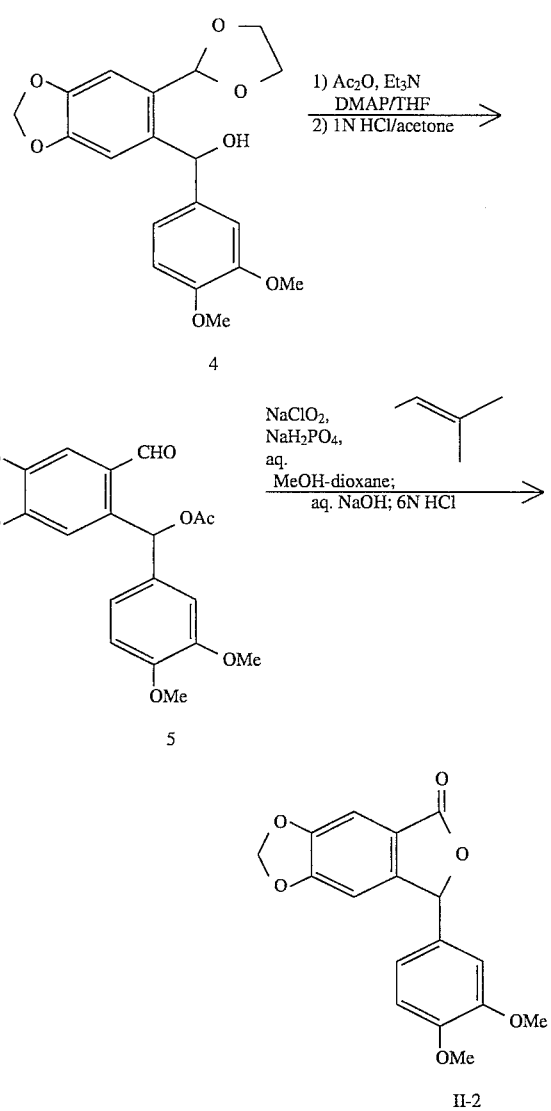

SYNTHETIC EXAMPLES OF THE COMPOUND III

PREPARATION 3

Synthesis of Methyl 4-Oxo-4-[4-(trifluoromethyl)phenyl]-2-butynoate: III-a

Step 1

Synthesis of methyl 4-[4-(trifluoromethyl)phenyl]-4-(trimethylsilyloxy)-2-butynoate: 8a Under nitrogen flow, a solution (61 ml; 100 mmoles) of 1.64M n-butyllithium in n-hexane was added dropwise to a solution of 21.1 ml (100 mmoles) of (TMS)$_2$NH in 100 ml of dry THF at −20° C. to −30° C. Under cooling in a dry ice-acetone bath, a solution of 8.41 g (100 mmoles) of methyl propiolate (compound 6) in 15 ml of dry THF was added dropwise to the reaction solution over 9 minutes. After completion of the addition, the reaction mixture was stirred for 36 minutes and a solution of 17.4 g (100 mmoles) of 4-(trifluoromethyl)benzaldehyde (compound 7a) in 60 ml of dry THF was added dropwise over 15 minutes. After stirring for additional 55 minutes, 14.0 ml (110 mmoles) of trimethylsilyl chloride was added to the mixture over 7 minutes. The mixture was stirred for additional 37 minutes, and the cooling bath was removed, then stirring was continued for 16 minutes. To the reaction mixture was added 100 ml of 1N hydrochloric acid and the mixture was extracted with ethyl acetate. The extract was washed with water and brine, dried over anhydrous magnesium sulfate, and concentrated in vacuo to give a crude product of the desired silyl ether (8a) as an oil. This was used for the next reaction without further purification.

Step 2

Synthesis of Compound III-a

Under cooling in an ice-bath, a 8N Jones' reagent (50 ml) was added dropwise to a solution of the crude product of silyl ether 8a obtained above in 170 ml of acetone over 15 minutes. After completion of the addition, the mixture was stirred for 35 minutes and then 11.4 ml (150 mmoles) of 2-propanol was added. The mixture was allowed to warm to room temperature while being stirring for 1 hour. The reaction mixture was filtered and the residual chromium sulfate was washed with acetone. The washing was combined with the reaction mixture, and the mixture was concentrated in vacuo. The residue was dissolved in 40 ml of ethyl acetate, 150 ml of water and 120 ml of n-hexane were added to the solution, and then the solution was extracted. The organic layer was washed with water and brine, dried over anhydrous magnesium sulfate and concentrated in vacuo. n-Hexane (80 ml) was added to the residue, the insoluble materials were filtered off, the filtrate was concentrated in vacuo and the residue was dried in vacuo at 40° C. for 30 minutes with stirring to give 21.6 g (84.6% from compound 7a) of the crude product of the desired compound III-a as an oil. When this was stored in a refrigerator overnight, it gave crystals with low melting point. However, this was used in the next reaction without further purification. Melting point: 28°–29° C. (methanol).

$^1$H-NMR:$\delta$(CDCl$_3$) 3.92 (3H, s) 7.80 (2H, d, J=8.2 Hz) 8.24 (2H, d, J=8.2 Hz).

PREPARATION 4

Synthesis of Methyl 4-(4-Chlorophenyl)-4-oxo-2-butynoate: III-b

The reaction was conducted in a procedure similar to that of Preparation 3 starting from 4-chlorobenzaldehyde (compound 7b) to give the desired compound III-b. Melting point: 49°–50° C.

$^1$H-NMR:$\delta$(CDCl$_3$) 3.90 (3H, s) 7.50 (2H, d, J=8.8 Hz) 8.05 (2H, d, J=8.8 Hz).

PREPARATION 5

Synthesis of Methyl 4-(3-Chlorophenyl)-4-oxo-2-butynoate: III-c

The reaction was conducted in a procedure similar to that of Preparation 3 starting from 3-chlorobenzaldehyde (compound 7c) to give the desired compound III-c. Melting point: 73°–75° C.

$^1$H-NMR:$\delta$(CDCl$_3$) 3.91 (3H, s) 7.48 (1 H, t, J=8.0 Hz) 7.62– 7.68 (1H, m) 7.97–8.09 (2H, m).

PREPARATION 6

Synthesis of Methyl 4-(2-Chlorophenyl)-4-oxo-2-butynoate: III-d

The reaction was conducted in a procedure similar to that of Preparation 3 starting from 2-chlorobenzaldehyde (compound 7d) to give the desired compound III-d. An oil.

$^1$H-NMR:$\delta$(CDCl$_3$) 3.89 (3H, s) 7.38–7.59 (3H, m) 8.01–8.09 (1H, m).

PREPARATION 7

Synthesis of Methyl 4-Oxo-4-phenyl-2-butynoate: III-e

The reaction was conducted in a procedure similar to that of Preparation 3 starting from benzaldehyde (compound 7e) to give the desired compound III-e. Melting point: 31°–35° C.

$^1$H-NMR:$\delta$(CDCl$_3$) 3.90 (3H, s) 7.47–7.58 (2H, m) 7.63–7.73 (1H, m) 8.09–8.17 (2H, m).

PREPARATION 8

Synthesis of Methyl 4-(4-Methoxyphenyl)-4-oxo-2-butynoate: III-f

The reaction was conducted in a procedure similar to that of Preparation 3 starting from 4-methoxybenzaldehyde (compound 7f) to give the desired compound III-f. Melting point: 67°–68° C.

$^1$H-NMR:$\delta$(CDCl$_3$) 3.89 (3H, s) 3.91 (3H, s) 6.98 (2H, d, J=9.0 Hz) 8.09 (2H, d, J=9.0 Hz).

PREPARATION 9

Synthesis of Methyl 4-(3-Methoxyphenyl)-4-oxo-2-butynoate: III-g

The reaction was conducted in a procedure similar to that of Preparation 3 starting from3-methoxybenzaldehyde (compound 7g) to give the desired compound III-g. Melting point: 32°–34° C.

$^1$H-NMR:$\delta$(CDCl$_3$) 3.87 (3H, s) 3.90 (3H, s) 7.18–7.25 (1H, m) 7.48 (1H, t, J=8.0 Hz) 7.56–7.61 (1H, m) 7.70–7.77 (1H, m).

PREPARATION 10

Synthesis of Methyl 4-(2-Methoxyphenyl)-4-oxo-2-butynoate: III-h

The reaction was conducted in a procedure similar to that of Preparation 3 starting from 3-methoxybenzaldehyde (compound 7h) to give the desired compound III-h. An oil.

$^1$H-NMR:$\delta$(CDCl$_3$) 3.87 (3H, s) 3.95 (3H, s) 6.98–7.10 (2H, m) 7.53–7.64 (1H, m) 7.97 (1H, dd, J=7.8 Hz, 1.8 Hz).

PREPARATION 11

Synthesis of Methyl 4-(2-Methylphenyl)-4-oxo-2-butynoate: III-i

The reaction was conducted in a procedure similar to that of Preparation 3 starting from 2-methylbenzaldehyde (compound 7i) to give the desired compound III-i. Melting point: 43°–45° C.

$^1$H-NMR:δ(CDCl$_3$) 2.63 (3H, s) 3.89 (3H, s) 7.25–7.56 (3H, m) 8.18 (1H, d, J=7.8 Hz).

The above reactions for Preparations 3 to 11 are expressed by the following scheme.

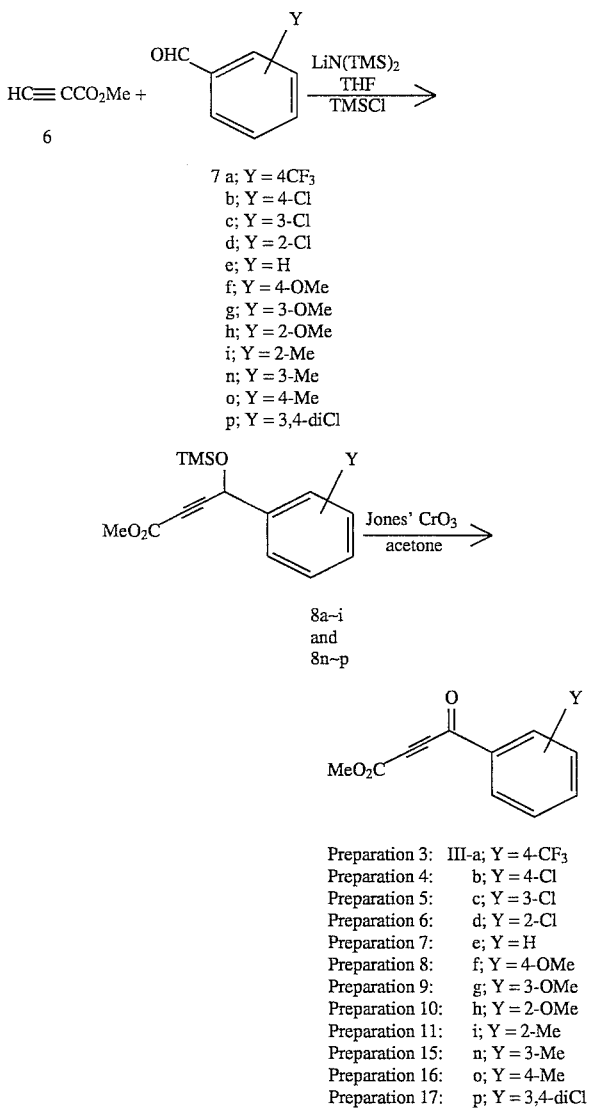

PREPARATION 12

Synthesis of Methyl 4-Cyclohexyl-4-oxo-2-butynoate: III-k

Step 1

Synthesis of Methyl 4-Cyclohexyl-4-hydroxy-2-butynoate: 10k.

Under nitrogen flow, a solution of methyl propiolate (compound 6) (1.68 g; 20.0 mmoles) in 4 ml of dry THF was added dropwise to a solution of 20.0 ml (20.0 mmoles) of 1M LiN(TMS)$_2$-THF in 40 ml of dry THF at −78° C. After completion of the addition, the reaction solution was stirred for 1 hour, and a solution of 2.24 g (20.0 mmoles) of cyclohexanecarboxyaldehyde (compound 9k) in 5 ml of dry THF was added dropwise thereto. The mixture was stirred for additional 1 hour, a saturated aqueous ammonium chloride was added to the reaction solution and the mixture was extracted with ethyl acetate. The extract was washed with water and brine, dried over anhydrous magnesium sulfate and concentrated in vacuo to give a crude product of the desired alcohol 10k as an oil. This was used in the next reaction without further purification.

Step 2

Synthesis of Compound III-k

A 8N Jones' reagent (10 ml) was added dropwise to a solution of the crude product of the alcohol 10k obtained above in 30 ml of acetone under cooling in an ice bath over 7 minutes. After completion of the addition, the mixture was stirred for 35 minutes. And then 5 ml of 2-propanol was added to the reaction solution and the mixture was allowed to warm to room temperature while being stirred for 1.5 hours. The reaction solution was filtered and the residual chromium sulfate was washed with acetone. The washing was combined with the reaction solution, and the mixture was concentrated in vacuo. Water and ethyl acetate were added to the resulting residue. The organic layer was washed with water and brine and dried over anhydrous magnesium sulfate. After concentration in vacuo, the residue was purified by a medium pressure silica gel column chromatography (60 g of SiO$_2$; ethyl acetate:n-hexane=1:10) to give 3.26 g (84% from compound 9k) of the desired compound III-k as an oil.

$^1$H-NMR:δ(CDCl$_3$) 1.10–2.03 (10H, m) 2.40–2.54 (1H, m) 3.85 (3H, s).

PREPARATION 13

Synthesis of Methyl 5-Ethyl-4-oxo-2-heptynoate: III-l

The reaction was conducted in a procedure similar to that of Preparation 12 starting from (2-ethyl)butyraldehyde (compound 9l) to give the desired compound, III-l, as an oil.

$^1$H-NMR:δ(CDCl$_3$) 0.91 (6H, t, J=7.4 Hz) 1.49–1.87 (4H, m) 2.36–2.51 (1H, m) 3.85 (3H, s).

PREPARATION 14

Synthesis of Methyl 6-Ethyl-4-oxo-2-octynoate: III-m

The reaction was conducted in a procedure similar to that of Preparation 12 starting from (3-ethyl)valeraldehyde (compound 9m) to give the desired compound, III-m, as an oil.

$^1$H-NMR:δ(CDCl$_3$) 0.88 (6H, t, J=7.2 Hz) 1.20–1.50 (4H, m) 1.93–2.01 (1H, m) 2.55 (2H, d, J=7.0 Hz) 3.85 (3H, s).

The above reactions for Preparations 12 to 14 are expressed by the following scheme.

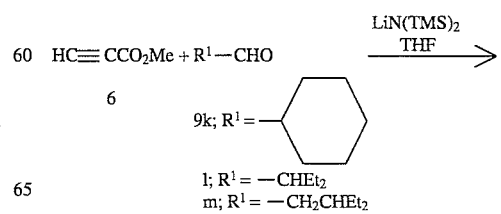

-continued

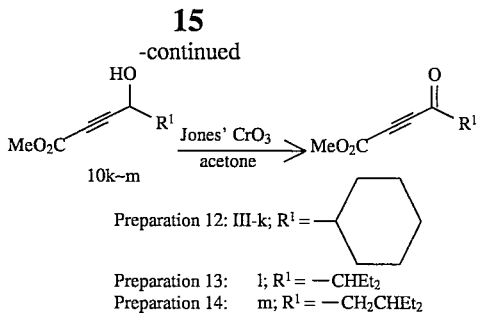

Preparation 12: III-k; $R^1 = $ —⬡

Preparation 13: l; $R^1 = $ —CHEt$_2$
Preparation 14: m; $R^1 = $ —CH$_2$CHEt$_2$

PREPARATION 15

Synthesis of Methyl 4-(3-Methylphenyl)-4-oxo-2-butynoate: III-n

The reaction was conducted in a procedure similar to that of Preparation 3 starting from 3-methylbenzaldehyde to give the desired compound. Melting point: 36°–38° C.

$^1$H-NMR:δ(CDCl$_3$) 2.44(3H,s), 3.90(3H,s), 7.36–7.52(2H,m), 7.89–7.96(2H,m).

PREPARATION 16

Synthesis of Methyl 4-(4-Methylphenyl)-4-oxo-2-butynoate: III-o

The reaction was conducted in a procedure similar to that of Preparation 3 starting from 4-methylbenzaldehyde to give the desired compound. Melting point: 44°–47° C.

$^1$H-NMR:δ(CDCl$_3$) 2.45(3H,s), 3.89(3H,s), 7.32(2H,d,J=8.2 Hz), 8.01(2H,d,J=8.2 Hz).

PREPARATION 17

Synthesis of Methyl 4-(3,4-Dichlorophenyl)-4-oxo-2-butynoate: III-p

The reaction was conducted in a procedure similar to that of Preparation 3 starting from 3,4-dichlorobenzaldehyde to give the desired compound. Melting point: 58°–59° C.

$^1$H-NMR:δ(CDCl$_3$) 3.92(3H,s), 7.63(2H,d,J=8.4 Hz), 7.95(1H,dd,J=8.4 Hz,2.0 Hz), 8.18(2H,d,J=2.0 Hz).

EXAMPLES FOR THE COMPOUNDS (I)

EXAMPLE 1

Synthesis of 1-(3,4-Dimethoxyphenyl)-4-hydroxy-2-(methoxycarbonyl)-3-[4-(trifluoromethyl)benzoyl]-6,7,8-trimethoxynaphthalene: I-a Step 1

Synthesis of 1-(3,4-Dimethoxyphenyl)-1,4-dihydro-2-(methoxycarbonyl)-3-[4-(trifluoromethyl)benzoyl]-6,7,8-trimethoxy-4-(trimethylsilyloxy)-1,4-epoxynaphthalene: IV-a Under nitrogen flow, a solution of 1.64M n-butyllithium in hexane (44.8 ml; 73.5 mmoles) was added dropwise to a solution of 15.5 ml (73.5 mmoles) of (TMS)$_2$NH in 90 ml of dry THF at –20° C.—30° C. A solution of 25.2 g (70.0 mmoles) of compound II-1 (Preparation 1) in 50 ml of dry methylene chloride was added dropwise over 25 minutes to the reaction solution under cooling by using a dry ice-acetone bath. After additional stirring for 30 minutes, 10.3 ml (81 mmoles) of trimethylsilyl chloride was added to the reaction solution over 5 minutes and the mixture was stirred for additional 1 hour. To the reaction solution was added a solution of 1.48 g (14 mmoles) of tert-butyl alcohol in 3 ml of dry THF and the mixture was stirred for 15 minutes. Finally, a solution of 21.6 g of the crude product of compound III-a (Preparation 3) in 50 ml of dry THF was added dropwise over 25 minutes and then the mixture was stirred for additional 25 minutes. To the reaction solution was added 75 ml of 1N hydrochloric acid and the mixture was extracted with ethyl acetate. The extract was washed with water and brine, dried over anhydrous magnesium sulfate and concentrated in vacuo to give a crude product of the desired silyl ether IV-a as an oil. This was used in the next reaction without further purification.

Step 2

Synthesis of 4-(3,4-Dimethoxyphenyl)-4-hydroxy-3-(methoxycarbonyl)-2-[4-(trifluoromethyl)benzoyl]-5,6,7-trimethoxy-1(4H)-naphthalenone: V-a A 10% sulfuric acid (15 ml) was added to a solution of the crude product of silyl ether IV-a obtained above in 250 ml of dioxane and the mixture was stirred for 1 hour 40 minutes. After evaporation of dioxane in vacuo, 100 ml of water was added to the residue and the mixture was extracted with ethyl acetate. The extract was washed with water and brine, and dried over anhydrous magnesium sulfate. After concentration in vacuo, the residue was crystallized from 300 ml of methanol to give 37.1 g (86.0% from compound II-1) of the diketone V-a. Melting point: 161°–163° C.

$^1$H-NMR:δ(CDCl$_3$) 3.26 (3H, s) 3.47 (3H, s) 3.87 (3H, s) 3.88 (3H, s) 3.92 (3H, s) 3.93 (3H, s) 5.39 (1H, s,-OH) 6.82 (2H, s) 7.10 (1H, s) 7.44 (1H,s) 7.71 (2H, d, J=8.4 Hz) 7.94 (2H, d, J=8.4 Hz).

Step 3

Synthesis of the Compound I-a

Under nitrogen flow, a solution of titanium trichloride in hydrochloric acid (75 ml) and 55 ml of methanol were added to a solution of 32.8 g (53.2 mmoles) of the diketone V-a obtained above in 160 ml of dioxane and the mixture was stirred at 50° C. for 1 hour. After evaporation of dioxane in vacuo, water and ethyl acetate were added to the residue and the mixture was extracted. The extract was washed with 1N hydrochloric acid, water and brine, and dried over anhydrous magnesium chloride. After concentration in vacuo, the residue was crystallized from 99% ethanol to give 23.1 g (72.4%) of the desired compound I-a. Melting point: 114°–117° C.

$^1$H-NMR:δ(CDCl$_3$) 2.69 (3H, s) 3.24 (3H, s) 3.83 (3H, s) 3.89 (3H, s) 3.92 (3H, s) 4.07 (3H, s) 6.76–6.84 (3H, m) 7.62–7.73 (4H, m) 7.76 (1H, s) 12.57 (1H, s); IR:ν(CHCl$_3$) 1737, 1711, 1605, 1580, 1511, 1488, 1461, 1433, 1410, 1373, 1323, 1171, 1135, 1064, 1017 cm$^{-1}$; Analysis calculated for C$_{31}$H$_{27}$F$_3$O$_9$: C 62.00%, H 4.53%, F 9.49%; Found: C 61.80%, H 4.57%, F 9.46%.

EXAMPLE 2

Synthesis of 3-(4-Chlorobenzoyl)-1-(3,4-dimethoxyphenyl)-4-hydroxy-2-(methoxycarbonyl)-6,7,8-trimethoxynaphthalene: I-b Step 1

Synthesis of 2-(4-Chlorobenzoyl)-4-(3,4-dimethoxyphenyl)-4-hydroxy-3-(methoxycarbonyl)-5,6,7-trimethoxy-1(4H)-naphthalenone: V-b The reactions were conducted in procedures similar to those of steps 1 and 2 in Example 1 starting from compound II-1 (Preparation 1) and compound III-b (Preparation 4) to give the desired diketone V-b. Melting point: 133°–134° C. (Methanol).

$^1$H-NMR:δ(CDCl$_3$) 3.26 (3H, s) 3.45 (3H, s) 3.86 (3H, s) 3.87 (3H, s) 3.92 (3H, s) 3.93 (3H, s) 5.39 (1H, br. s) 6.81 (2H, br. s) 7.07 (1H, s) 7.41 (2H, d, J=8.4 Hz) 7.45 (1H, s) 7.76 (2H, d, J=8.4 Hz).

Step 2

Synthesis of the Compound I-b

The reaction was conducted in a procedure similar to that of step 3 in Example 1 starting from compound V-b obtained above to give the desired compound I-b. Melting point: 167°–169° C. (methanol).

$^1$H-NMR:δ(CDCl$_3$) 2.79 (3H, s) 3.24 (3H, s) 3.83 (3H, s) 3.90 (3H, s) 3.92 (3H, s) 4.06 (3H, s) 6.78–6.86 (3H, m) 7.38 (2H, d, J=8.8 Hz) 7.58 (2H, d, J=8.8 Hz) 7.73 (1 H, s) 12.30 (1 H, s); IR:ν(CHCl$_3$) 1739, 1712, 1602, 1583, 1512, 1489, 1462, 1411, 1131, 1090, 1056 cm$^{-1}$; Analysis calculated for C$_{30}$H$_{27}$ClO$_9$: C 63.55%, H 4.80%, Cl 6.25%; Found: C 63.65%, H 4.84%, Cl 6.54%.

EXAMPLE 3

Synthesis of 3-(3-Chlorobenzoyl)-1-(3,4-dimethoxyphenyl)-4-hydroxy-2-(methoxycarbonyl)-6,7,8-trimethoxynaphthalene: I-c Step 1

Synthesis of 2-(3-Chlorobenzoyl)-4-(3,4-dimethoxyphenyl)-4-hydroxy-3-(methoxycarbonyl)-5,6,7-trimethoxy-1(4H)naphthalenone: V-c The reactions were conducted in procedures similar to those of steps 1 and 2 in Example 1 starting from compound II-1 (Preparation 1) and compound III-c (Preparation 5) to give the desired diketone V-c. Melting point: 135°–136° C. (Methanol).

$^1$H-NMR:δ(CDCl$_3$) 3.26 (3H, s) 3.47 (3H, s) 3.86 (3H, s) 3.87 (3H, s) 3.92 (3H, s) 3.94 (3H, s) 5.39 (1H, s) 6.78–6.90 (2H, m) 7.07 (1H, d, J=1.6 Hz) 7.37 (1H, t, J=7.6 Hz) 7.45 (1H, s) 7.50–7.56 (1H, m) 7.68 (1H, dt, J=7.6 Hz, 1.4 Hz) 7.81 (1H, t, J=1.6 Hz).

Step 2

Synthesis of the Compound I-c

The reaction was conducted in a procedure similar to that of step 3 in Example 1 starting from compound V-c obtained above to give the desired compound I-c. Melting point: 141°–142° C. (Methanol).

$^1$H-NMR:δ(CDCl$_3$) 2.78 (3H, s) 3.24 (3H, s) 3.84 (3H, s) 3.89 (3H, s) 3.91 (3H, s) 4.06 (3H, s) 6.76–6.86 (3H, m) 7.29–7.64 (4H, m) 7.74 (1H, s) 12.45 (1H, s); IR:ν(CHCl$_3$) 1735, 1711, 1603, 1581, 1514, 1487, 1461, 1434, 1413, 1371, 1220, 1133, 1055 cm$^{-1}$; Analysis calculated for C$_{30}$H$_{27}$ClO$_9$: C 63.55%, H 4.80%, Cl 6.25%; Found: C 63.38%, H 4.86%, Cl 6.46%.

EXAMPLE 4

Synthesis of 3-(2-Chlorobenzoyl)-1-(3,4-dimethoxyphenyl)-4-hydroxy-2-(methoxycarbonyl)-6,7,8-trimethoxynaphthalene: I-d Step 1

Synthesis of 2-(2-Chlorobenzoyl)-4-(3,4-dimethoxyphenyl)-4-hydroxy-3-(methoxycarbonyl)-5,6,7-trimethoxy-1(4H)-naphthalenone: V-d The reactions were conducted in procedures similar to those of steps 1 and 2 in Example 1 starting from compound II-1 (Preparation 1) and compound III-d (Preparation 6) to give the desired diketone V-d. An oil.

1H-NMR:δ(CDCl$_3$) 3.23 (3H, s) 3.54 (3H, s) 3.84 (3H, s) 3.86 (3H, s) 3.90 (3H, s) 3.92 (3H, s) 5.31 (1H, s) 6.76–6.86 (2H, m) 7.00 (1H, br.s) 7.30–7.54 (4H, m) 7.70–7.81 (1H, s).

Step 2

Synthesis of Compound I-d

The reaction was conducted in a procedure similar to that of step 3 in Example 1 starting from compound V-d obtained above to give the desired compound I-d. Melting point: 157°–158° C. (methanol).

$^1$H-NMR:δ(CDCl$_3$) 2.74 (3H, s) 3.23 (3H, s) 3.80 (3H, s) 3.87 (3H, s) 3.91 (3H, s) 4.06 (3H, s) 6.77 (3H, s) 7.21–7.44 (4H, m) 7.79 (1H, s) 13.70 (1H, s); IR:ν(CHCl$_3$) 1735, 1713, 1601, 1513, 1487, 1461, 1437, 1412, 1375, 1306, 1283, 1238, 1133, 1065, 1047,1028 cm$^{-1}$; Analysis calculated for C$_{30}$H$_{27}$ClO$_9$: C 63.55%, H 4.80%, Cl 6.25%; Found: C 63.35%, H 4.84%, Cl 6.13%.

EXAMPLE 5

Synthesis of 3-Benzoyl-1-(3,4-dimethoxyphenyl)-4-hydroxy-2-(methoxycarbonyl)-6,7,8-trimethoxynaphthalene: I-e Step 1

Synthesis of 2-benzoyl-4-(3,4-dimethoxyphenyl)-4-hydroxy-3-(methoxycarbonyl)-5,6,7-trimethoxy-1(4H)-naphthalenone: V-e The reactions were conducted in procedures similar to those of steps 1 and 2 in Example 1 starting from compound II-1 (Preparation 1) and compound III-e (Preparation 7) to give the desired diketone V-e. Melting point: 152°–153° C. (methanol).

$^1$H-NMR:δ(CDCl$_3$) 3.26 (3H, s) 3.41 (3H, s) 3.86 (3H, s) 3.87 (3H, s) 3.91 (3H, s) 3.93 (3H, s) 5.44 (1H, br. s) 6.87–6.90 (2H, m) 7.08 (2H, d, J=0.4 Hz) 7.38–7.63 (4H, m) 7.83 (2H, d, J=7.0 Hz).

Step 2

Synthesis of the Compound I-e

The reaction was conducted in a procedure similar to that of step 3 in Example 1 starting from compound V-e obtained above to give the desired compound I-e. Melting point: 139°–140° C. (ethyl acetate-isopropyl ether).

$^1$H-NMR:δ(CDCl$_3$) 2.71 (3H, s) 3.24 (3H, s) 3.83 (3H, s) 3.89 (3H, s) 3.91 (3H, s) 4.06 (3H, s) 6.78–6.83 (3H, m) 7.34–7.68 (5H, m) 7.41 (1H, s) 12.44 (1H, s); IR:ν(nujol) 1727, 1598, 1573, 1509, 1486, 1409, 1213, 1125, 1049, 1022 cm$^{-1}$; Analysis calculated for $C_{30}H_{28}O_9$: C 67.66%, H 5.30%; Found: C 67.62%, H 5.39%.

EXAMPLE 6

Synthesis of 1-(3,4-Dimethoxyphenyl)-4-hydroxy-3-(4-methoxybenzoyl)-2-(methoxycarbonyl)-6,7,8-trimethoxynaphthalene: I-f Step 1

Synthesis of 4-(3,4-dimethoxyphenyl)-4-hydroxy-2-(4-methoxybenzoyl)-3-(methoxycarbonyl)-5,6,7-trimethoxy-1(4H)-naphthalenone: V-f The reactions were conducted in procedures similar to those of steps 1 and 2 in Example 1 starting from compound II-1 (Preparation 1) and compound III-f (Preparation 8) to give the desired diketone V-f. Melting point: 134°–136° C. (methanol).

$^1$H-NMR:δ(CDCl$_3$) 3.26 (3H, s) 3.41 (3H, s) 3.85 (3H, s) 3.86 (6H, s) 3.91 (3H, s) 3.93 (3H, s) 5.44 (1H, s) 6.78–6.95 (4H, m) 7.06 (1H, d, J=1.8 Hz) 7.47 (1H, s) 7.80 (2H, d, J=8.8 Hz).

Step 2

Synthesis of the Compound I-f

The reaction was conducted in a procedure similar to that of step 3 in Example 1 starting from compound V-f obtained above to give the desired compound I-f. Melting point: 151°–152° C. (methylene chloride-isopropyl ether).

$^1$H-NMR:δ(CDCl$_3$) 2.83 (3H, s) 3.24 (3H, s) 3.83 (6H, s) 3.90 (3H, s) 3.91 (3H, s) 4.05 (3H, s) 6.80–6.93 (5H, m) 7.66 (2H, d, J=6.9 Hz) 7.71 (1H, s) 11.97 (1H, s); IR:ν(CHCl$_3$) 1738, 1713, 1600, 1510, 1461, 1412, 1168, 1055, 1028 cm$^{-1}$; Analysis calculated for $C_{31}H_{30}O_{10}$: C 66.19%, H 5.38%; Found: C 66.46%, H 5.48%.

EXAMPLE 7

Synthesis of 1-(3,4-Dimethoxyphenyl)-4-hydroxy-3-(3-methoxybenzoyl)-2-(methoxycarbonyl)-6,7,8-trimethoxynaphthalene: I-g Step 1

Synthesis of 4-(3,4-Dimethoxyphenyl)-4-hydroxy-2-(3-methoxybenzoyl)-3-(methoxycarbonyl)-5,6,7-trimethoxy-1(4H)-naphthalenone: V-g The reactions were conducted in procedures similar to those of steps 1 and 2 in Example 1 starting from compound II-1 (Preparation 1) and compound III-g (Preparation 9) to give the desired diketone V-g. Melting point: 146°–148° C. (methanol).

$^1$H-NMR:δ(CDCl$_3$) 3.26 (3H, s) 3.42 (3H, s) 3.81 (3H, s) 3.86 (3H, s) 3.87 (3H, s) 3.91 (3H, s) 3.93 (3H, s) 5.43 (1H, br.s) 6.77–6.91 (2H, m) 7.06–7.14 (2H, m) 7.25–7.44 (3H, m) 7.47 (1H, s).

Step 2

Synthesis of the Compound I-g

The reaction was conducted in a procedure similar to that of step 3 in Example 1 starting from compound V-g obtained above to give the desired compound I-g. Melting point: 119°–121° C. (isopropyl ether).

$^1$H-NMR:δ(CDCl$_3$) 2.77 (3H, s) 3.24 (3H, s) 3.83 (6H, s) 3.89 (3H, s) 3.91 (3H, s) 4.06 (3H, s) 6.77–6.85 (3H, m) 7.00–7.07 (1H, m) 7.16–7.34 (3H, m) 7.74 (1H, s) 12.41 (1H, s); IR:ν(CHCl$_3$) 1738, 1711, 1598, 1581, 1511, 1487, 1460, 1410, 1130, 1055 cm$^{-1}$. Analysis calculated for $C_{31}H_{30}O_{10}$: C 66.19%, H 5.38%; Found: C 66.14%, H 5.40%.

EXAMPLE 8

Synthesis of 1-(3,4-Dimethoxyphenyl)-4-hydroxy-3-(2-methoxybenzoyl)-2-(methoxycarbonyl)-6,7,8-trimethoxynaphthalene: I-h Step 1

Synthesis of 4-(3,4-Dimethoxyphenyl)-4-hydroxy-2-(4-methoxybenzoyl)-3-(methoxycarbonyl)-5,6,7-trimethoxy-1(4H)-naphthalenone: V-h The reactions were conducted in procedures similar to those of steps 1 and 2 in Example 1 starting from compound II-1 (Preparation 1) and compound III-h (Preparation 10) to give the desired diketone V-h. Melting point: 168°–169° C. (methanol).

$^1$H-NMR:δ(CDCl$_3$) 3.24 (3H, s) 3.45 (3H, s) 3.63 (3H, s) 3.84 (3H, s) 3.86 (3H, s) 3.91 (3H, s) 3.94 (3H, s) 5.36 (1H, s) 6.72–6.84 (2H, m) 6.92 (1H, d, J=8.0 Hz) 7.01–7.14 (2H, m) 7.48 (1H, s) 7.46– 7.56 (1.H, m) 7.95 (1H, dd, J=7.8 Hz, 1.8 Hz).

Step 2

Synthesis of Compound I-h

The reaction was conducted in a procedure similar to that of step 3 in Example 1 starting from compound V-h obtained above to give the desired compound I-h. Melting point: 183°–184° C. (methylene chloride-isopropyl ether).

$^1$H-NMR:δ(CDCl$_3$) 2.70 (3H, s) 3.23 (3H, s) 3.78 (3H, s) 3.80 (3H, s) 3.87 (3H, s) 3.91 (3H, s) 4.06 (3H, s) 6.76 (3H, br.s) 6.84–7.00 (2H, m) 7.27–7.43 (2H, m) 7.78 (1H, s) 13.68 (1H, s); IR:ν(CHCl$_3$) 1738, 1714, 1601, 1582, 1514, 1490, 1463, 1412, 1135, 1058 cm$^{-1}$; Analysis calculated for $C_{31}H_{30}C_{10}$: C 66.19%, H 5.38%; Found: C 66.30%. H 5.44%.

EXAMPLE 9

Synthesis of 1-(3,4-Dimethoxyphenyl)-4-hydroxy-2-(methoxycarbonyl)-3-(2-methylbenzoyl)-6,7,8-trimethoxynaphthalene: I-i Step 1

Synthesis of 4-(3,4-dimethoxyphenyl)-4-hydroxy-3-(methoxycarbonyl)-2-(2-methylbenzoyl)-5,6,7-trimethoxy-1(4H)-naphthalenone: V-i The reactions were conducted in procedures similar to those of steps 1 and 2 in Example 1 starting from compound II-1 (Preparation 1) and compound III-i (Preparation 11) to give the desired diketone V-i. Melting point: 137–140° C. (methanol).

$^1$H-NMR:δ(CDCl$_3$) 2.63 (3H, s) 3.25 (3H, s) 3.47 (3H, s) 3.70 (3H, s) 3.86 (6H, s) 3.90 (3H, s) 3.91 (3H, s) 5.39 (1H, br.s) 6.77–6.87 (2H, m) 6.99–7.54 (6H, m).

Step 2

Synthesis of Compound I-i

The reaction was conducted in a procedure similar to that of step 3 in Example 1 starting from compound V-i obtained above to give the desired compound I-i. Melting point: 159°–160° C. (methylene chloride-isopropyl ether).

$^1$H-NMR:δ(CDCl$_3$) 2.40 (3H, s) 2.65 (3H, s) 3.23 (3H, s) 3.81 (3H, s) 3.87 (3H, s) 3.91 (3H, s) 4.06 (3H, s) 6.77 (3H, br.s) 7.08–7.35 (4H, m) 7.77 (1H, s) 13.57 (1H, s); IR:ν(CHCl$_3$) 1740, 1712, 1604, 1583, 1514, 1489, 1462, 1411, 1138, 1056 cm$^{-1}$; Analysis calculated for C$_{31}$H$_{30}$O$_9$: C 68.12%, H 5.53%; Found: C 68.03%, H 5.52%.

EXAMPLE 10

Synthesis of 1-(3,4-Dimethoxyphenyl)-4-hydroxy-2 -(methoxycarbonyl)-6,7-methylenedioxy-3-[4- (trifluoromethyl)benzoyl] -naphthalene: I-j Step 1

Synthesis of 4-(3,4-Dimethoxyphenyl)-4-hydroxy-3 -(methoxycarbonyl)-6,7-methylenedioxy-2-[4- (trifluoromethyl)benzoyl] -1(4H)-naphthalenone: V-j The reactions were conducted in procedures similar to those of steps 1 and 2 in Example 1 starting from compound II-2 (Preparation 2) and compound III-a (Preparation 3) to give the desired diketone V-j.

$^1$H-NMR:δ(CDCl$_3$) 3.43 (3H, s) 3.86 (3H, s) 3.90 (3H, s) 5.35 (1 H, s) 6.00 (1H, s) 6.04 (1H, s) 6.82–6.99 (3H, m) 7.03 (1H, s) 7.41 (1H, s) 7.75 (2H, d, J=8.2 Hz) 8.00 (2F!, d, J=8.2 Hz).

Step 2

Synthesis of Compound I-j

The reaction was conducted in a procedure similar to that of step 3 in Example 1 starting from compound V-j obtained above to give the desired compound I-j. Melting point: 208°–209° C. (methylene chloride-methanol).

$^1$H-NMR:δ(CDCl$_3$) 2.76 (3H, s) 3.83 (3H, s) 3.93 (3H, s) 6.11 (2H, s) 6.72 (1H, d, J=1.8 Hz) 6.79 (1H, dd, J=8.2 Hz, 1.8 Hz) 6.88 (1H, s) 6.92 (1H, d, J=8.2 Hz) 7.66 (1H, d, J=8.4 Hz) 7.74 (1H, d, J=8.4 Hz) 7.84 (1H, s) 12.40 (1H, s); IR:ν(CHCl$_3$) 1732, 1713, 1620, 1586, 1515, 1460, 1321, 1240, 1173, 1135, 1039 cm$^{-1}$; Analysis calculated for C$_{29}$H$_{21}$F$_3$O$_8$: C 62.82%, H 3.82%, F 10.28%; Found: C 62.53%, H 3.93%, F 10.20%.

EXAMPLE 11

Synthesis of 3-(Cyclohexanecarbonyl)-1-(3,4-dimethoxyphenyl)- 4-hydroxy-2-(methoxycarbonyl)-6,7,8- trimethoxynaphthalene: I-k Step 1

Synthesis of 2-(Cyclohexanecarbonyl)-4-(3,4 -dimethoxyphenyl)-4-hydroxy-3-(methoxycarbonyl)- 5,6,7 -trimethoxy-1(4H)-naphthalenone: V-k The reactions were conducted in procedures similar to those of steps 1 and 2 in Example 1 starting from compound II-1 (Preparation 1) and compound III-k (Preparation 12), which was followed by purification over silica gel chromatography and crystallization to give the desired diketone V-k. Melting point: 173°–174° C. (methylene chloride-methanol).

$^1$H-NMR:δ(CDCl$_3$) 1.04–2.08 (10H, m) 2.63–2.82 (1H, m) 3.22 (3H, s) 3.66 (3H, s) 3.82 (3H, s) 3.84 (3H, s) 3.89 (3H, s) 3.97 (3H, s) 5.29 (1H, s) 6.77 (2H, br.s) 6.93 (1H, s) 7.49 (1H, s).

Step 2

Synthesis of Compound I-k

The reaction was conducted in a procedure similar to that of step 3 in Example 1 starting from compound V-k obtained above to give the desired compound I-k. Melting point: 150°–151° C. (methylene chloride-methanol).

$^1$H-NMR:δ(CDCl$_3$) 1.15–1.90 ( 10H, m) 2.70–2.90 ( 1 H, m) 3.24 (3H, s) 3.44 (3H, s) 3.86 (3H, s) 3.89 (3H, s) 3.93 (3H, s) 4.03 (3H, s) 6.81–6.87 (3H, m) 7.71 (1H, s) 13.99 (1H, s); IR:ν(Nujol) 1714, 1606, 1580, 1516, 1489, 1410, 1240, 1197, 1142, 1107, 1063, 1027, 1004 cm$^{-1}$; Analysis calculated for C$_{30}$H$_{34}$O$_9$: C 66.90%, H 6.36%; Found: C 66.82%, H 6.38%.

EXAMPLE 12

Synthesis of 1-(3,4-Dimethoxyphenyl)-3-(2-ethyl-1 -oxobutyl)-4-hydroxy-2-(methoxycarbonyl)-6,7,8- trimethoxynaphthalene: I-l Step 1

Synthesis of 4-(3,4-Dimethoxyphenyl)-2-(2-ethyl-1 -oxobutyl)-4-hydroxy-3-(methoxycarbonyl)-5,6,7- trimethoxy-1(4H)-naphthalenone: V-l The reactions were conducted in procedures similar to those of step 1 in Example 11 starting from the compound II-1 (Preparation 1) and compound III-l (Preparation 13) to give the desired diketone V-l. Melting point: 115°–116° C. (methylene chloride-methanol).

$^1$H-NMR:δ(CDCl$_3$) 0.91 (3H, t, J=7.4 Hz) 0.93 (3H, t, J=7.4 Hz) 1.40–1.82 (4H, m) 2.85–2.99 (1H, m) 3.22 (3H, s) 3.68 (3H, s) 3.82 (3H, s) 3.85 (3H, s) 3.90 (3H, s) 3.97 (3H, s) 5.29 (1H, br.s) 6.70– 6.82 (2H, m) 6.91 (1H, d, J=1.6 Hz) 7.50 (1H, s).

Step 2

Synthesis of Compound I-l

The reaction was conducted in a procedure similar to that of step 3 in Example 1 starting from compound V-l obtained above to give the desired compound I-l. Melting point: 113°–115° C. (acetone-n-hexane).

$^1$H-NMR:δ(CDCl$_3$) 0.82 (3H, t, J=8 Hz) 0.83 (3H, t, J=8 Hz) 1.42–1.60 (2H, m) 1.64–1.81 (2H, m) 2.78–2.90 (1H, m) 3.24 (3H, s) 3.42 (3H, s) 3.86 (3H, s) 3.89 (3H, s) 3.93 (3H, s) 4.03 (3H, s) 6.81–6.87 (3H, m) 7.72 (1H, s) 14.18 (1H, s); IR:ν(CHCl$_3$) 1730, 1606, 1575, 1523, 1490, 1463, 1412, 1137, 1062, 1029 cm$^{-1}$; Analysis calculated for $C_{29}H_{34}O_9$: C 66.14%, H 6.51%; Found: C 66.11%, H 6.60%.

EXAMPLE 13

Synthesis of 1-(3,4-Dimethoxyphenyl)-3-(3-ethyl-1-oxopentyl)-4-hydroxy-2-(methoxycarbonyl)-6,7,8-trimethoxynaphthalene: I-m Step 1

Synthesis of 4-(3,4-Dimethoxyphenyl)-2-(3-ethyl-1-oxopentyl)-4-hydroxy-3-(methoxycarbonyl)-5,6,7-trimethoxy-1(4H)-naphthalenone: V-m The reactions were conducted in procedures similar to those of step 1 in Example 11 starting from compound II-1 (Preparation 1) and compound III-m (Preparation 14) to give the desired diketone V-m. Melting point: 141°–142° C. (methylene chloride-methanol).

$^1$H-NMR:$\delta$(CDCl$_3$) 0.86 (3H, t, J=7.4 Hz) 0.88 (3H, t, J=7.4 Hz) 1.28–1.44 (4H, m) 1.82–1.99 (1FI, m) 2.62–2.83 (2H, m) 3.22 (3H, s) 3.67 (3H, s) 3.83 (3H, s) 3.84 (3H, s) 3.89 (3H, s) 3.96 (3H, s) 5.29 (1H, s) 6.68–6.80 (2H, m) 6.96 (1H, d, J=1.8 Hz) 7.49 (1H, s).

Step 2

Synthesis of Compound I-m

The reaction was conducted in a procedure similar to that of step 3 in Example 1 starting from compound V-m obtained above to give the desired compound I-m. Melting point: 128.5°–129.5° C. (methylene chloride-methanol).

$^1$H-NMR:$\delta$(CDCl$_3$) 0.83 (6H, t, J=7 Hz) 1.20–1.42 (4H, m) 1.96–2.12 (1H, m) 2.73 (2H, d, J=6 Hz) 3.25 (3H, s) 3.44 (3H, s) 3.86 (3H, s) 3.89 (3H, s) 3.93 (3H, s) 4.04 (3H, s) 6.78–6.90 (3H, m) 7.73 (1H, s) 14.38 (1 H, s); IR:v(CHCl$_3$) 2968, 1729, 1606, 1576, 1514, 1489, 1464, 1412, 1139, 1064, 1028 cm$^{-1}$; Analysis calculated for $C_{30}H_{36}O_9$: C 66.65%, H 6.71%; Found: C 66.62%, H 6.71%.

EXAMPLE 14

Synthesis of Compound I-a (Which Is Prepared in Example 1) Directly from Compound IV-a Step 1

Synthesis of 1-(3,4-Dimethoxyphenyl)-1,4-dihydro-2-(methoxycarbonyl)-3-[(4-(trifluoromethyl)benzoyl]-6,7,8-trimethoxy-4-(trimethylsilyloxy)-1,4-epoxynaphthalene: IV-a The reaction was conducted in a procedure similar to the step 1 in Example 1 starting from 9.00 g (25.0 mmoles) of compound II-1 (Preparation 1) and 7.04 g (27.5 mmoles) of compound III-a (Preparation 3) to give the crude product of the desired compound IV-a. This was used in the next reaction without further purification.

Step 2

Synthesis of Compound I-a

Under nitrogen flow, a solution of titanium trichloride in hydrochloric acid (30.8 ml) and 30 ml of methanol were added to a solution of the crude product of compound IV-a obtained above in 100 ml of dioxane and the mixture was stirred at 50° C. for 3 hours. After evaporation of dioxane in vacuo, water and ethyl acetae were added to the residue and the mixture was extracted. The extract was washed with 1N hydrochloric acid, water and brine, and dried over anhydrous magnesium sulfate. After concentration in vacuo, the residue was crystallized from 99% ethanol to give 9.25 g (61.5%) of the desired compound I-a. Physical properties of the resulting compound were entirely identical with those of the compound obtained in Example 1.

EXAMPLE 15

Synthesis of 1-(3,4-Dimethoxyphenyl)-4-hydroxy-2-(methoxycarbonyl)-3-(3-methylbenzoyl)-6,7,8-trimethoxynaphthalene: I-n Step 1

Synthesis of 4-(3,4-Dimethoxyphenyl)-4-hydroxy-3-(methoxycarbonyl)-2-(3-methylbenzoyl)-5,6,7-trimethoxy-1(4H)-naphthalenone: V-n The reactions were conducted in procedures similar to those of steps 1 and 2 in Example 1 starting from compound II-1 (Preparation 1) and compound III-n (Preparation 15) to give the desired diketone V-n. Melting point: 143°–144° C. (methanol).

$^1$H-NMR:$\delta$(CDCl$_3$) 2.37(3H,s), 3.26(3H,s), 3.42(3H,s), 3.86(3H,s), 3.87(3H,s), 3.91(3H,s), 3.93(3H,s), 5.45(1H, br.s), 6.77–6.90(2H,m), 7.08(1H,d,J=2.0 Hz), 7.27–7.40(2H,m), 7.46(1H,s), 7.57–7.69(2H,m).

Step 2

Synthesis of Compound I-n

The reaction was conducted in a procedure similar to that of step 3 in Example 1 starting from compound V-n obtained above to give the desired compound I-n. Melting point: 125°–126° C. (methylene chloride-isopropyl alcohol).

$^1$H-NMR:$\delta$(CDCl$_3$) 2.36(3H,s), 2.72(3H,s), 3.23(3H,s), 3.83(3H,s), 3.89(3H,s), 3.91(3H,s), 4.06(3H,s), 6.77–6.84(3H,m), 7.25–7.47(4H,m), 7.74(1H,s), 12.47(1H, s); IR:v(CHCl$_3$) 1739, 1713, 1601, 1583, 1514, 1488, 1462, 1411, 1130, 1057, 1027 cm$^{-1}$; Analysis calculated for $C_{31}H_{30}O_9$: C 68.12%, H 5.53%; Found: C 67.93%, H 5.52%.

EXAMPLE 16

Synthesis of 1-(3,4-dimethoxyphenyl)-4-hydroxy-2-(methoxycarbonyl)-3-(4-methylbenzoyl)-6,7,8-trimethoxynaphthalenone: I-o Step 1

Synthesis of 4-(3,4-Dimethoxyphenyl)-4-hydroxy-3-(methoxycarbonyl)-2-(4-methylbenzoyl)-5,6,7-trimethoxy-1(4H)-naphthalene: V-o The reactions were conducted in procedures similar to those of steps 1 and 2 in Example 1 starting from compound II-1 (Preparation 1) and compound III-o (Preparation 16) to give the desired diketone IV-o. Melting point: 107°–110° C. (methanol).

$^1$H-NMR:$\delta$(CDCl$_3$) 2.40(3H,s), 3.27(3H,s), 3.42(3H,s), 3.87(6H,s), 3.92(3H,s), 3.94(3H,s), 5.45(1H,br.s), 6.78–6.92(2H,m), 7.07(1H,d,J=1.6 Hz), 7.24(2H,d,J=8.0 Hz), 7.48(1H,s), 7.73(2H,d,J= 8.0 Hz).

Step 2

Synthesis of Compound I-o

The reaction was conducted in a procedure similar to that of step 3 in Example 1 starting from compound V-o obtained above to give the desired compound I-o. Melting point: 165°–167° C. (methylene chloride-methanol).

$^1$H-NMR:δ(CDCl$_3$) 2.37(3H,s), 2.76(3H,s), 3.24(3H,s), 3.83(3H,s), 3.89(3H,s), 3.91 (3H,s), 4.06(3H,s), 6.78–6.86(3H,m), 7.20(2H,d,J=8.0 Hz), 7.55(2H,d,J=8.0 Hz), 7.73(1H,s), 12.26(1H,s); IR:ν(CHCl$_3$) 1739, 1713, 1605, 1585, 1514, 1489, 1464, 1411, 1131, 1056 cm$^{-1}$; Analysis calculated for C$_{31}$H$_{30}$O$_9$: C 68.12%, H 5.53%; Found: C 68.31%, H 5.61%.

EXAMPLE 17

Synthesis of 3-(3,4-Dichlorobenzoyl)-1-(3,4-dimethoxyphenyl)-4-hydroxy-2-(methoxycarbonyl)-6,7,8-trimethoxynaphthalene: I-p Step 1

Synthesis of 2-(3,4-Dichlorobenzoyl)-4-(3,4-dimethoxyphenyl)-4-hydroxy-3-(methoxycarbonyl)-5,6,7-trimethoxy-1(4H)-naphthalenone: V-p The reactions were conducted in procedures similar to those of steps 1 and 2 in Example 1 starting from compound (Preparation 1) and compound III-p (Preparation 17) to give the desired diketone V-p. Melting point: 160°–161° C. (methanol).

$^1$H-NMR:δ(CDCl$_3$) 3.25(3H,s), 3.50(3H,s), 3.86(3H,s), 3.87(3H,s), 3.92(3H,s), 3.94(3H,s), 5.38(1H,br.s), 6.81(2H, s), 7.07(1H,s), 7.44(1H,s), 7.52(1H,d,J=8.2 Hz), 7.63(1H, dd,J=8.2 Hz,2.0 Hz), 7.90(1H,d,J=2.0 Hz).

Step 2

Synthesis of Compound I-p

The reaction was conducted in a procedure similar to that of step 3 in Example 1 starting from compound V-p obtained above to give the desired compound I-p. Melting point: 139°–141° C. (methanol).

$^1$H-NMR:δ(CDCl$_3$) 2.82(3H,s), 3.27(3H,s), 3.84(3H,s), 3.90(3H,s), 3.92(3H,s), 4.06(3H,s), 6.74–6.86(3H,m), 7.48(2H,s), 7.73(2H,s) IR:ν(CHCl$_3$) 1735, 1710, 1603, 1583, 1513, 1487, 1461, 1434, 1412, 1372, 1306, 1283, 1237, 1131, 1056, 1029 cm$^{-1}$; Analysis calculated for C$_{30}$H$_{26}$Cl$_2$O$_9$: C 59.91%, H 4.36%, Cl 11.79%; Found: C 59.88%, H 4.43%, Cl 11.66%.

The compounds prepared in the above examples are listed in the following tables.

TABLE 1

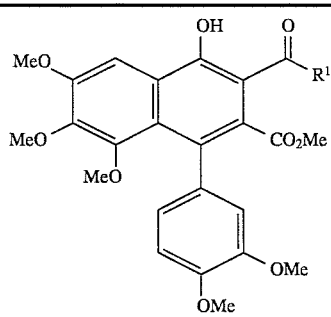

TABLE 1-continued

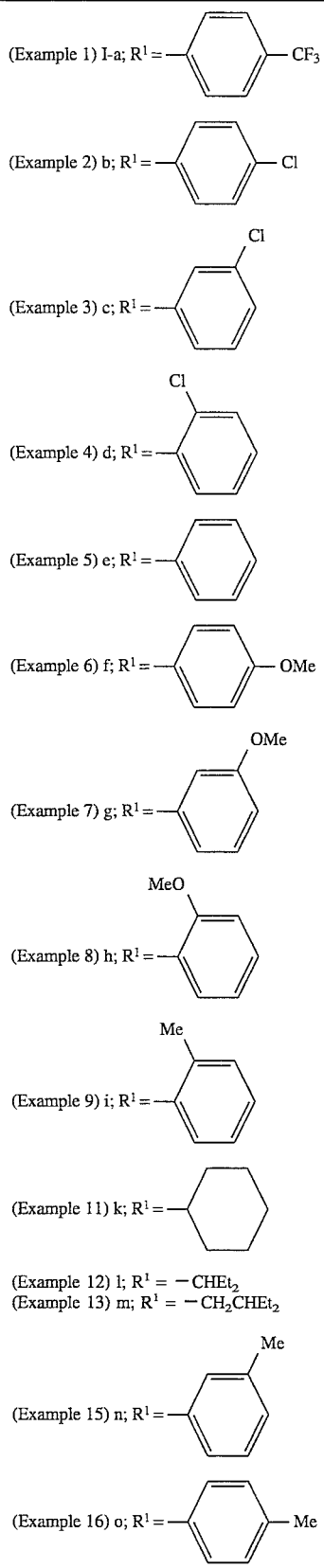

TABLE 1-continued

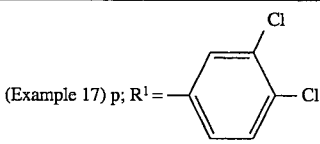

(Example 17) p; R¹ =

TABLE 2

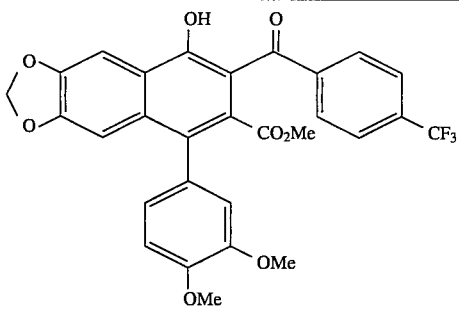

(Example 10) I-j

Effect of the Invention

The process of the present invention permits efficient synthesis of lignan analogs. In particular, the present process permits synthesis of the lignan analogs having an aryl ketone chain with good regioselectivity, and therefore, the present invention is useful in an industrial scale.

Pharmacological experiments were conducted using the compounds obtained in Examples 1 and 2.

EXPERIMENT 1

Inhibitory Action against Oxidative Modification of LDL

Testing and Evaluating Methods

Experiments were conducted as follows according to the method of Kita, et al. described in proceedings of the National Academy of Sciences, USA, volume 84, pages 5928 (1987).

First, LDL was separated from the blood of New Zealand White rabbits fed with a feed containing 0.5% of cholesterol for three weeks and dissolved in phosphate-buffered physiological saline (final LDL concentration: 0.2 mg protein/ml). To this was added an ethanolic solution of each test compound, then cupric sulfate was added thereto (final $Cu^{2+}$ concentration: 0.5 µM) and the mixture was incubated at 37° C. for 24 hours.

The amount of lipid peroxides in each of the incubated solutions was measured as thiobarbituric acid reacting substances (TBA reactive substances) and, from the regression line of the inhibitory rate for oxidative modification of LDL and the concentration of the compound, the 50% inhibiting concentration ($IC_{50}$) was calculated. Quantitative determination of the TBA reactive substances was conducted by measuring the TBA reactive substances in the supernatant (prepared by removing protein from the incubated solution) by means of TBA method.

The result is shown in Table 3 thereinafter.

The $IC_{50}$ values of the compounds obtained by the method of the present invention were not more than 10 µM and, accordingly, the compounds are understood to exhibit strong antioxidative action against LDL.

EXPERIMENT 2

Cholesterol-lowering Action

Testing and Evaluating Methods

Male ICR mice (body weight: 30–40 grams) were freely fed for seven days with a feed containing 1% of cholesterol and 0.5% of sodium cholate to which 0.12% of the test compound was added (no such a compound was added for the control group), then blood was collected from the mice and the total cholesterol in serum was measured by the method of Allain described in Clinical Chemistry, volume 20, page 470 (1974).

Total amount of VLDL cholesterol and LDL cholesterol was calculated by subtracting the amount of HDL cholesterol from the amount of total cholesterol. The amount of the HDL cholesterol was measured by the method of Ash and Hentschel described in Clinical Chemistry, volume 24, page 2180 (1978).

Cholesterol lowering action of the test compound was evaluated from the cholesterol lowering rate calculated from the following expressions.

Total cholesterol lowering rate =

{1 − [(total cholesterol in the group with the test compound)/

(total cholesterol in the control group)]} × 100

(VLDL + LDL) cholesterol lowering rate =

{1 − [(VLDL + LDL cholesterol in the group with the test compound)/

(VLDL + LDL cholesterol in the control group)] × 100

The result is given in Table 3.

TABLE 3

| Example No. | LDL-Oxidation Inhibiting $IC_{50}$ (µM) | Total Cholesterol Lowering Rate (%) | (VLDL + LDL) Cholesterol Lowering Rate (%) |
|---|---|---|---|
| 1 | 1.52 | 22 | 61 |
| 2 | 1.42 | 28 | 74 |

Both compounds tested exhibited excellent lowering action for (VLDL+LDL) cholesterol and do not show a decrease in HDL cholesterol and, therefore, the compounds obtained by the present invention are understood to exhibit strong and selective cholesterol lowering action.

We claim:

1. A process for preparing a compound represented by formula (I)

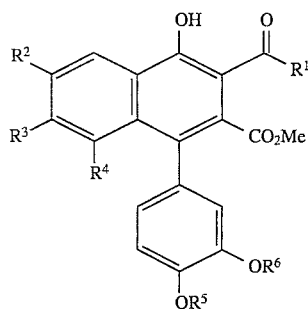

(I)

in which $R^1$ is alkyl, cycloalkyl, cycloalkyl-lower alkyl, aralkyl, or optionally-substituted aryl;

each of $R^2$ and $R^3$ is lower alkoxy or $R^2$ and $R^3$ are combined together to form an alkylenedioxy;

$R^4$ is lower alkoxy or hydrogen; and each of $R^5$ and $R^6$ is lower alkyl;

which process is characterized by that a lactone compound represented by the formula (II)

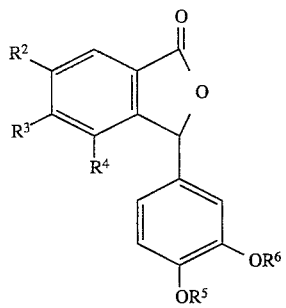

(II)

in which $R^2$, $R^3$, $R^4$, $R^5$, and $R^6$ are as defined above, is allowed to react with a compound of the formula: $R^7Cl$, wherein $R^7$ is tri (lower alkyl)silyl, in the presence of a base, then the resulting compound is subjected to addition reaction with an acetylenic compound of the formula (III)

(III)

in which $R^1$ is as defined above, to give a compound represented by the formula (IV)

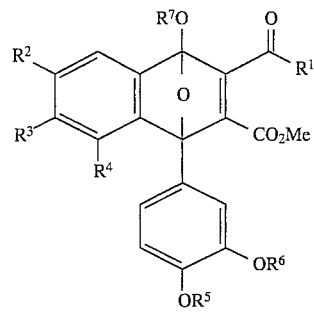

(IV)

in which $R^1$, $R^2$, $R^3$, $R^4$, $R^5$, $R^6$ and $R^7$ are as defined above, which is then reduced.

2. The process of claim 1 in which the tri(lower alkyl) silyloxy group: $OR^7$ in the compound represented by the formula (IV) is deprotected, and the resulting compound is reduced.

3. The process of claim 1 or 2 in which the reduction is carried out using a metal or a metal salt in the presence of an acid.

4. The process of claim 1 or 2 in which $R^1$ is (1) $C_1$ to $C_6$ alkyl, (2) $C_5$ to $C_7$ cycloalkyl, (3) $C_5$ to $C_7$ cycloalkyl ($C_1$ to $C_6$ alkyl), or (4) phenyl which is optionally mono- or di-substituted with halogen, trihalomethyl, lower alkoxy or lower alkyl.

5. The process of claim 4 in which $R^1$ is phenyl which is mono-substituted with halogen, trihalomethyl, lower alkoxy or lower alkyl.

6. The process of claim 1 or 2 in which $R^2$, $R^3$ and $R^4$ are methoxy.

7. The process of claim 3 in which $R^2$, $R^3$, and $R^4$ are methoxy.

8. The process of claim 4 in which $R^2$, $R^3$, and $R^4$ are methoxy.

9. The process of claim 5 in which $R^2$, $R^3$, and $R^4$ are methoxy.

* * * * *